US00PP31289P3

(12) United States Plant Patent
Park et al.

(10) Patent No.: US PP31,289 P3
(45) Date of Patent: Dec. 31, 2019

(54) ***CITRUS RETICULATA* BLANCO PLANT NAMED 'TAMNANEUNBONG'**

(50) Latin Name: ***Citrus reticulata* Blanco**
Varietal Denomination: Tamnaneunbong

(71) Applicant: THE RURAL DEVELOPMENT ADMINISTRATION, REPUBLIC OF KOREA, Chungcheongnam-Do (KR)

(72) Inventors: Jae-Ho Park, Seogwipo-si (KR); Su-Hyun Yun, Jeollabuk-Do (KR); Dong-Hoon Lee, Gyeonggi-Do (KR); Sang-Woog Koh, Jeju-Do (KR); Hyun-Joo An, Seogwipo-si (KR); I-Ung Yang, Seogwipo-si (KR)

( * ) Notice: Subject to any disclaimer, the term of this patent is extended or adjusted under 35 U.S.C. 154(b) by 0 days.

(21) Appl. No.: 14/756,932

(22) Filed: Oct. 30, 2015

(65) Prior Publication Data

US 2017/0127585 P1 May 4, 2017

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./156, 201
See application file for complete search history.

(56) References Cited

PUBLICATIONS

Korea Seed & Variety Service website—citation for regestration No. 5070. http://www.seed.go.kr/english/function/system_06_view.jsp?appl_idty=84400. Accessed May 1, 2017. 1 page.*

* cited by examiner

*Primary Examiner* — Susan McCormick Ewoldt
*Assistant Examiner* — Karen M Redden
(74) *Attorney, Agent, or Firm* — Baker Donelson

(57) ABSTRACT

A new and distinct *Citrus reticulate* Blanco plant named Tamnaneunbong, characterized by its upright plant type and strong vigor, short oval ovary shape, germination state in middle of April, blooming state in late May, fruits start coloring in late October, mature state in late March, acidity of the fruit juice at about 1.51%, leaf length at about 10.1 cm and leaf width at about 4.3 cm, and length of leaf petiole at about 3.6 cm.

2 Drawing Sheets

Latin name of the genus and species of the plant claimed: *Citrus reticulata* Blanco.

Variety denomination: 'Tamnaneunbong'.

BACKGROUND OF THE INVENTION

The new and distinct cultivar is a product of a breeding program by the inventors. This cultivar was developed by embryo sac culture. The embryo sac culture of 'Shiranui' (not patented) was carried out in 2000. The characteristic investigation of these nucellar seedlings was done from 2007 to 2010 in a greenhouse. The first screening was carried out in 2007, and the last screening was carried out in 2010. One new variety was picked and named 'Tamnaneunbong'.

The somatic cells of the nucellar tissue can also develop into embryos, called nucellar embryos, and then germinated into a plurality of nucellar seedings. The candidate varity is developed from the nucellar embryos of the femle parent. The variety was asexually propagated by grafting onto 'Satsuma' rootstock (or trifoliate orange rootstock) in Jeju-do, Korea for three generations and there was no genetic variation. The observed plant retains its distinctive characteristics and reproduces true to type in successive generations. Therefore, its traits are stable. The rootstock of 'Satsuma' is the tangerine tree and tangerine has no patent status.

The fruit characteristics of 'Tamnaneunbong' are in the table below. The test carried out from 2007 to 2010. 'Shiranui' was 5 years old in 2007. The 'Tamnaneunbong' was the nucellar seedling in this table.

TABLE 1

Fruit Characteristics

| Survey date (yy.mm.dd) | Variety | Fruit weight (g) | Flesh rate (%) | Fruit shape index | Peak height ( mm) |
|---|---|---|---|---|---|
| 07.1.24 | Tamnaneunbong | 268.4 | 77.5 | 94 | 15.6 |
| | Shiranui | 315.2 | 69.4 | 100 | 13.8 |
| 08.2.14 | Tamnaneunbong | 254.8 | 75.7 | 89 | 12.8 |
| | Shiranui | 172.4 | 72.4 | 98 | 4.5 |
| 09.2.17 | Tamnaneunbong | 364.8 | 72.6 | 93 | 17.0 |
| | Shiranui | 322.4 | 75.6 | 92 | 15.1 |
| 10.2.24 | Tamnaneunbong | 240.3 | — | — | — |
| | Shiranui | 157.0 | — | — | — |

| Survey date (yy.mm.dd) | Variety | Thickness of the skin ( mm) | Seed grain number | Sugar (°Bx) | Acid-ity (%) | Sugar acid ratio |
|---|---|---|---|---|---|---|
| 7.1.24 | Tamnaneun-bong | 2.9 | 0 | 14.4 | 1.28 | 11.24 |
| | Shiranui | 5.3 | 0 | 12.4 | 1.14 | 10.92 |
| 8.2.14 | Tamnaneun-bong | 3.7 | 0 | 13.6 | 1.44 | 9.43 |
| | Shiranui | 4.3 | 0 | 12.8 | 1.32 | 9.71 |
| 9.2.17 | Tamnaneun-bong | 4.2 | 0 | 15.3 | 1.28 | 11.97 |
| | Shiranui | 4.1 | 0 | 13.7 | 1.14 | 11.98 |

TABLE 1-continued

| Fruit Characteristics | | | | | | |
|---|---|---|---|---|---|---|
| 10.2.24 | Tamnaneunbong | — | 0 | 15.3 | 1.46 | 10.47 |
| | Shiranui | — | 0 | 12.2 | 1.46 | 8.35 |

Fruit shape index = The transverse diameter ÷ The longitudinal diameter × 100

Additional fruit characteristics of 'Tamnaneunbong' are in the table below. 'Shiranui' was 8 years old in 2010. The 'Tamnaneunbong' was grafted onto five years old 'Shiranui' three years ago.

TABLE 2

| Additional Fruit Characteristics | | | | | |
|---|---|---|---|---|---|
| Survey date (yy.mm.dd) | Variety | Fruit weight (g) | Flesh rate (%) | Fruit shape index | Peak height (mm) |
| 10.1.27 | Tamnaneunbong | 280.9 | 77.7 | 95 | 10.7 |
| | Shiranui | 255.6 | 77.0 | 97 | 9.2 |
| 10.3.4 | Tamnaneunbong | 237.7 | 76.5 | 93 | — |
| | Shiranui | 258.8 | 73.0 | 93 | — |

| Survey date (yy.mm.dd) | Variety | Thickness of the skin (mm) | Seed grain number | Sugar (°Bx) | Acidity (%) | Sugar acid ratio |
|---|---|---|---|---|---|---|
| 10.1.27 | Tamnaneunbong | 3.6 | 0 | 15.3 | 1.45 | 10.67 |
| | Shiranui | 3.8 | 0 | 14.5 | 1.20 | 12.08 |
| 10.3.4 | Tamnaneunbong | 3.8 | 0 | 17.5 | 1.51 | 11.74 |
| | Shiranui | 4.1 | 0 | 16.0 | 1.22 | 13.17 |

SUMMARY OF THE INVENTION

The cultivar 'Tamnaneunbong' has not been observed under every possible environmental conditions. Therefore, there may be variations in the phenotype due to varying environmental conditions such as temperature, day length and light intensity. However, the genotype will not vary.

The following traits have been repeatedly observed and are determined to be the characteristics of the new cultivar of *Citrus reticulata* Blanco. These attributes in combination distinguish 'Tamnaneunbong' from and all other varieties of *Citrus reticulata* Blanco known to Inventors.

1. The plant type of 'Tamnaneunbong' is upright and the tree vigor is strong.
2. Ovary shape of 'Tamnaneunbong' is short oval.
3. The fruit color is orange.
4. Germination stage is in the middle of April.
5. Blooming stage is in late May.
6. Fruits start coloring in late October.
7. The mature stage is in late March.
8. Acidity of the fruit juice is about 1.51%.
9. The leaf length is about 10.1 cm and the leaf width is about 4.3 cm.
10. The length of leaf petiole is about 3.6 cm.

Plants of the new cultivar 'Tamnaneunbong' are similar to plants of the seed parent 'Shiranui' in most horticultural characteristics, however, the plants of the new cultivar 'Tamnaneunbong' produce fruit that are more acidic than the parent. The fruit produced by 'Tamnaeunbong' start coloring in late October and mature in late March.

The new cultivar differs from the closest comparable plants as shown in the tables below:

TABLE 3

| Comparison With Closest Variety | | | |
|---|---|---|---|
| Denomination of similar variety | Characteristic in which the similar variety is different | The expression of the characteristic: Similar variety | The expression of the characteristic: Candidate variety |
| Shiranui | Plant: type | medium | upright |
| | Plant: tree vigor | medium | strong |
| | Ovary: shape | depressed globose | short oval |
| | Fruit juice: acidity | 1.22% | 1.51% |
| | Leaf: leaf length | 8.0 cm | 10.1 cm |
| | Leaf: leaf width | 3.0 cm | 4.3 cm |
| | Leaf petiole: length | 4.1 mm | 3.6 mm |
| | Fruits start coloring | in early October | in late October |
| | Mature stage | in early March | in late March |

TABLE 4

| Comparison With Closest Variety | | | | | | |
|---|---|---|---|---|---|---|
| | | Forms of Expression | | | | |
| NO | Characteristics | 1 | 2 | 3 | 4 | 5 |
| 1 | Plant: Type | upright | | | | medium |
| 2 | Young shoot: thickness | thin | | | | medium |
| 3 | Young shoot: length | very short | | short | | medium |
| 4 | Stem: internode length | very short | | short | | medium |
| 5 | leaf: color | light green | | | | green |
| 6 | leaf: length | very short | | short | | medium |
| 7 | leaf: width | very narrow | | narrow | | medium |
| 8 | leaf: length/width ratio | small | | | | medium |
| 9 | leaf: thickness | thin | | | | medium |
| 10 | Leaf petiole: length | very short | | short | | medium |
| 11 | Leaf petiole: thickness | thin | | | | medium |
| 12 | Flower: petal length | very short | | short | | medium |
| 13 | Flower: petal width | very narrow | | narrow | | medium |
| 14 | Ovary: shape | Long oval | globose | depressed globose | ap-planate | cylinder |
| 15 | Flower: activity pollen | absent | | | | |
| 16 | Fruit: length/width ratio | small | | | | medium |
| 17 | Fruit: surface color | green | yellowish green | light yellow | medium yellow | yellowish orange |
| 18 | Fruit: surface roughness | smooth | | | | |
| 19 | Fruit: fresh color | with white | light green | light yellow | medium yellow | light orange |
| 20 | Fruit: skin thickness | thin | | | | medium |
| 21 | Fruit juice: total soluble solids | low | | | | medium |
| 22 | Fruit juice: acidity | low | | | | medium |

TABLE 4-continued

| Comparison With Closest Variety | | | | |
|---|---|---|---|---|
| 23 | Mature stage | very early | early | medium |
| 24 | Parthenocarpy | absent | | |
| 25 | Self-in-compatibility | absent | | |
| 26 | Tree vigor | weak | | medium |

| | | Forms of Expression | | | |
|---|---|---|---|---|---|
| NO | Characteristics | 6 | 7 | 8 | 9 |
| 1 | Plant: Type | | | | pendulous |
| 2 | Young shoot: thickness | | | | thick |
| 3 | Young shoot: length | | long | | very long |
| 4 | Stem: internode length | | long | | very long |
| 5 | leaf: color | | | | dark green |
| 6 | leaf: length | | long | | very long |
| 7 | leaf: width | | broad | | very broad |
| 8 | leaf: length/width ratio | | | | large |
| 9 | leaf: thickness | | | | thick |
| 10 | Leaf petiole: length | | long | | very long |
| 11 | Leaf petiole: thickness | | | | thick |
| 12 | Flower: petal length | | long | | very long |
| 13 | Flower: petal width | | broad | | very broad |
| 14 | Ovary: shape | short oval | gourd | | |
| 15 | Flower: activity pollen | | | | present |
| 16 | Fruit: length/width ratio | | | | large |
| 17 | Fruit: surface color | medium orange | dark orange | red with orange | red |
| 18 | Fruit: surface roughness | | | | rough |
| 19 | Fruit: fresh color | medium orange | dark orange | red | purple |
| 20 | Fruit: skin thickness | | | | thick |
| 21 | Fruit juice: total soluble solids | | | | high |
| 22 | Fruit juice: acidity | | | | high |
| 23 | Mature stage | | late | | very late |
| 24 | Parthenocarpy | | | | present |
| 25 | Self-incompatibility | | | | present |
| 26 | Tree vigor | | | | strong |

| | | Application variety: Tamnaneunbong | | Similar variety: Shiranui | |
|---|---|---|---|---|---|
| NO | Characteristics | No | Data | No | Data |
| 1 | Plant: Type | 1 | | 5 | |
| 2 | Young shoot: thickness | 5 | 2.6 mm | 1 | 1.9 mm |
| 3 | Young shoot: length | 7 | 20.0 cm | 7 | 15.9 cm |
| 4 | Stem: internode length | 5 | 1.9 cm | 5 | 1.5 cm |
| 5 | leaf: color | 5 | | 5 | |
| 6 | leaf: length | 7 | 10.1 cm | 5 | 8.0 cm |
| 7 | leaf: width | 5 | 4.3 cm | 3 | 3.2 cm |
| 8 | leaf: length/width ratio | 7 | 2.4 | 7 | 2.5 |
| 9 | leaf: thickness | 5 | 0.032 mm | 5 | 0.031 mm |
| 10 | Leaf petiole: length | 3 | 3.6 mm | 5 | 4.1 mm |
| 11 | Leaf petiole: thickness | 5 | 1.9 mm | 5 | 1.7 mm |
| 12 | Flower: petal length | 5 | 16.3 mm | 5 | 15.0 mm |
| 13 | Flower: petal width | 7 | 8.1 mm | 7 | 6.7 mm |
| 14 | Ovary: shape | 6 | | 3 | |
| 15 | Flower: activity pollen | 1 | | 1 | |

TABLE 4-continued

| Comparison With Closest Variety | | | | | |
|---|---|---|---|---|---|
| 16 | Fruit: length/width ratio | 3 | 0.95 | 3 | 0.95 |
| 17 | Fruit: surface color | 4 | | 4 | |
| 18 | Fruit: surface roughness | 9 | | 9 | |
| 19 | Fruit: fresh color | 5 | | 5 | |
| 20 | Fruit: skin thickness | 5 | 3.7 mm | 5 | 3.9 mm |
| 21 | Fruit juice: total soluble solids | 5 | 17.5°Bx | 5 | 16.0°Bx |
| 22 | Fruit juice: acidity | 7 | 1.51% | 5 | 1.22% |
| 23 | Mature stage | 7 | | 7 | |
| 24 | Parthenocarpy | 9 | | 9 | |
| 25 | Self-incompatibility | 9 | | 9 | |
| 26 | Tree vigor | 9 | | 5 | 30 |

BRIEF DESCRIPTION OF THE DRAWINGS

The accompanying colored photographs illustrate the overall appearance and distinct characteristics of the new *Citrus reticulata* Blanco 'Tamnaneunbong' showing colors as true as is reasonably possible with colored reproduction of this type. These photos were taken in 2010 in Korea. Colors in the photographs may differ slightly from the color values cited in the detailed botanical description which accurately describes the color of the 'Tamnaneunbong'.

DETAILED BOTANICAL DESCRIPTION

Figure 1:
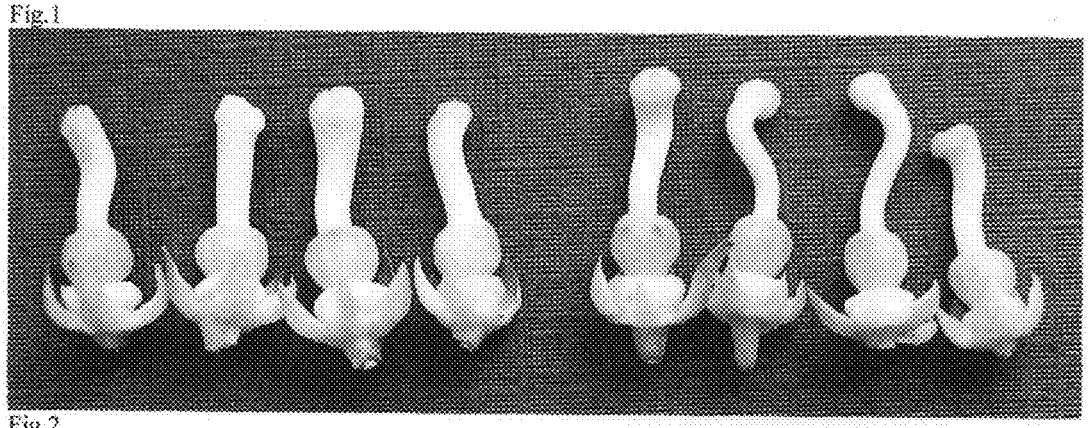
FIG. 1 provides multiple views of the ovaries of the fruits harvested from 'Tamnaneunbong' and 'Shiranui'. The four ovaries on the left of the photograph are ovaries of the fruit harvested from 'Shiranui' while the four ovaries on the right of the photograph are ovaries of the fruit harvested from 'Tamnaneunbong'. All are from ten years old plants.
Figure 2:
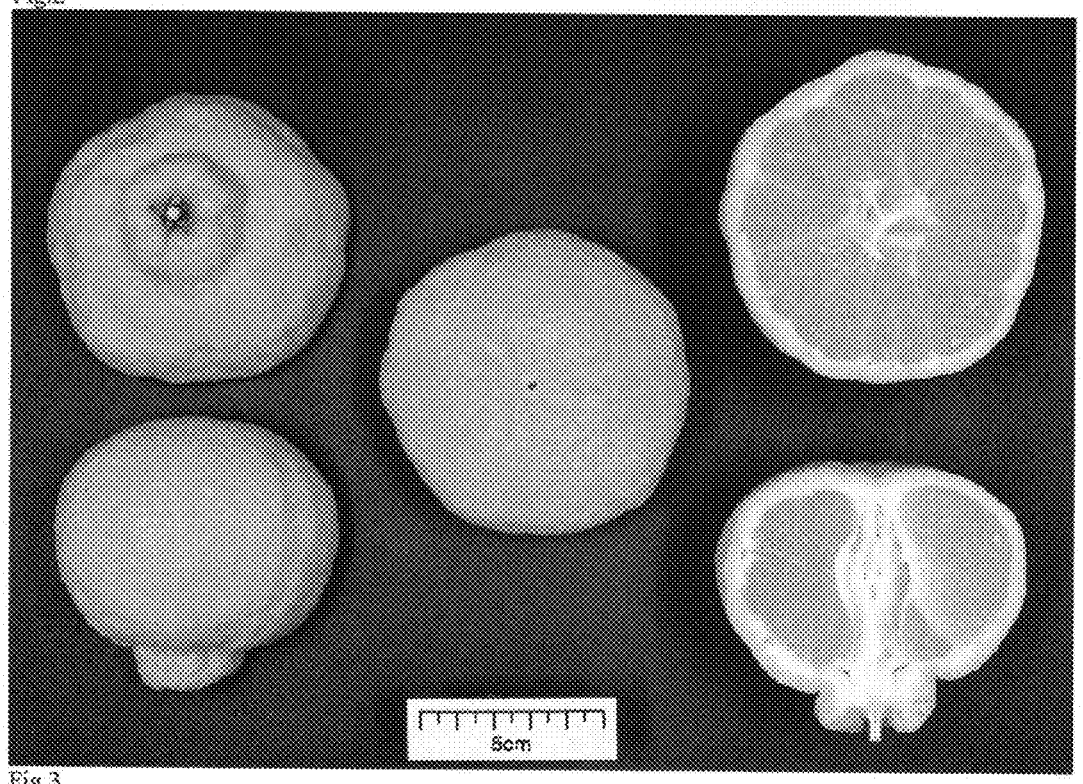
FIG. 2 provides multiple views of typical fruits harvested from ten years old 'Tamnaneunbong' plants. Top, bottom and side views of the whole, unpeeled fruit is shown as well as two cross-sectional views of the inside of the fruit.
Figure 3:
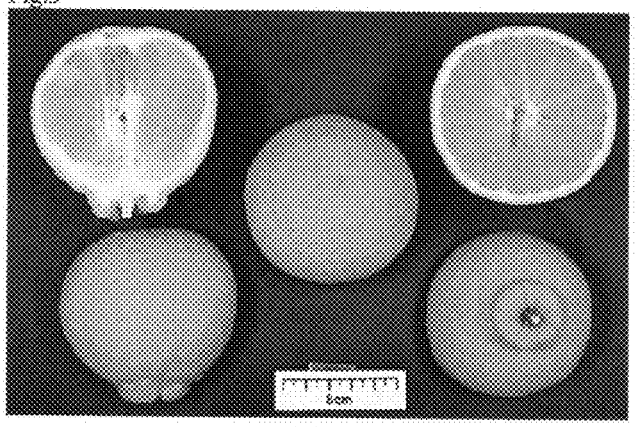
FIG. 3 provides multiple views of typical fruits harvested from ten years old 'Shiranui' plants. Top, bottom and side views of the whole, unpeeled fruit is shown as well as two cross-sectional views of the inside of the fruit
Figure 4:
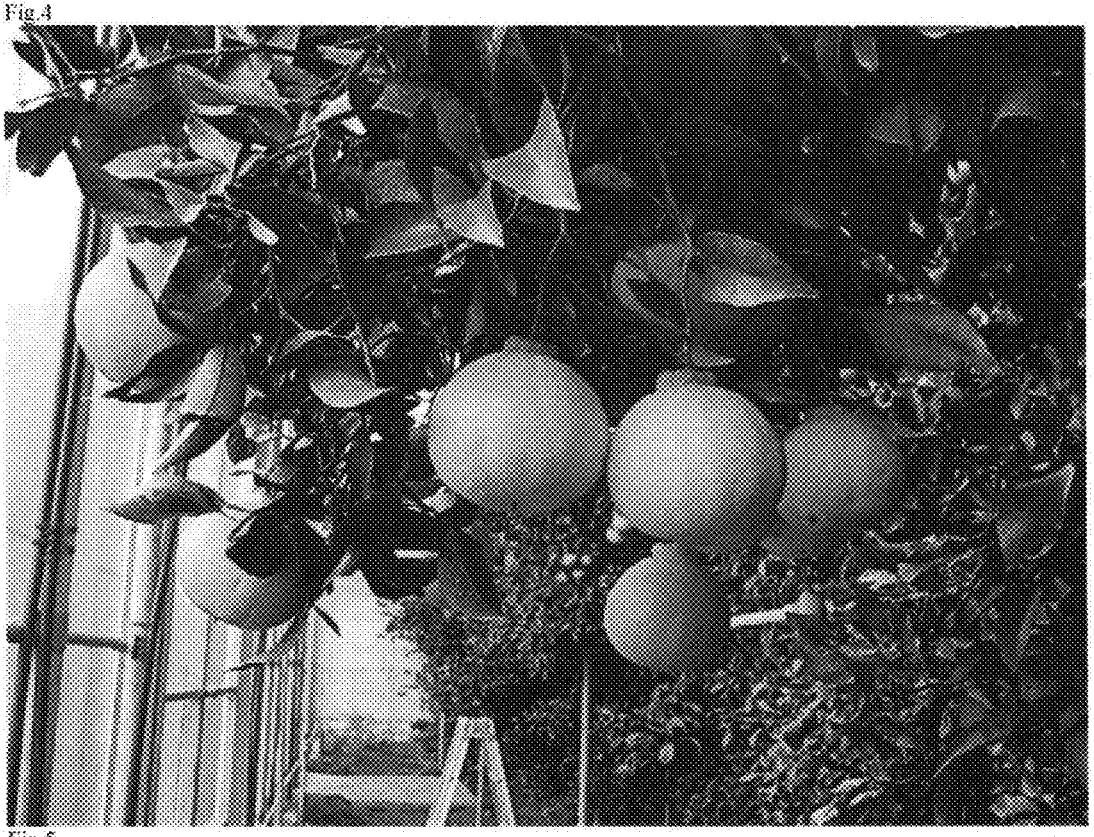
FIG. 4 illustrates in full color typical foliage and fruits of 'Tamnaneunbong' on the ten years old tree.
Figure 5:
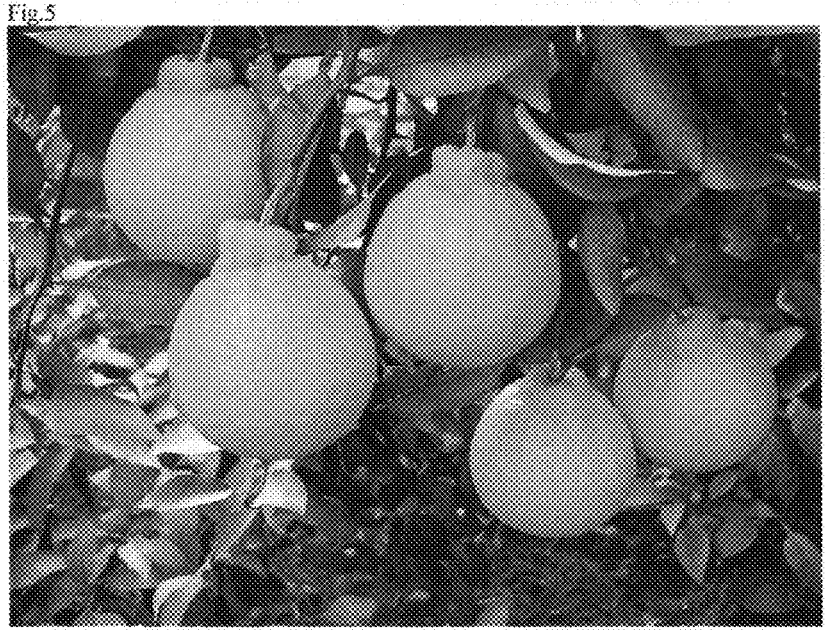
FIG. 5 illustrates in full color typical foliage and fruits of 'Shiranui' on the ten years old tree.

In the following description of the new cultivar 'Tamnaneunbong' as taken from tests carried from 2007 to 2010. The characteristics of the overall 'Tamnaneunbong' plant include strong tree vigor, erect-type tree form, fruit shape which is oblate, orange pericarp color, orange flesh color, strong fragrance and moderate oil glands. The following observations and measurements describe 'Tamnaneunbong' plants grown in Korea.

The Colour Chart used in the identification of colors described herein is The R.H.S. Colour Chart of The Royal Horticultural Society, 2007, Fifth edition, except where general color terms of ordinary significance are used.

TABLE 5

Color of 'Tamnaneunbong' and 'Shiranui'

| | Tamnaneunbong | | Shiranui | |
|---|---|---|---|---|
| | COLOR | | COLOR | |
| Fruit: surface color | Yellow orange | Yellow orange RHS 25A | Yellow orange | Yellow orange RHS 25A |
| Fruit: flesh color | Light orange | RHS orange 26B | Light orange | RHS orange 26B |
| leaf: upper surface color of mature leaves | Green | RHS green 137A | Green | RHS green 137A |
| leaf: lower surface color of mature leaves | Green | RHS green 137A | Green | RHS green 137A |
| Leaf: upper surface color of young leaves | Green | RHS green 143A | | |
| Leaf: lower surface color of young leaves | Green | RHS 144A | | |
| Stem: bark color | Greyed-Green | RHS Greyed-Green 197A | | |
| Flower: color of opened flower | White | RHS NN 155 White C | | |
| Petal: upper surface color | White | RHS NN 155 White C | | |
| Petal: lower surface color | White | RHS NN 155 White C | | |
| Seed: seed color | No Seed | | | |

Propagation: 'Tamnaneunbong' is typically grafted onto rootstock of 'Shiranui'.

Plant:

*Age of plant described.*—Approximately 3 years old.

*Vigor.*—Strong.

*Plant posture.*—Upright.

Foliage:

*Young shoot thickness.*—2.6 mm.

*Young shoot length.*—20.0 cm.

*Stem internode length.*—1.9 cm.

*Leaf color.*—Green.

*Leaf length.*—10.1 cm.

*Leaf width.*—4.3 cm.

*Leaf length/width ratio.*—2.4.

*Leaf thickness.*—0.032 mm.

*Leaf petiole length.*—3.6 mm.

*Leaf petiole thickness.*—1.9 mm.

*Leaf arrangement.*—Alternate.

*Venation pattern.*—Pinnate.

*Leaf margins.*—Crenate.

*Texture of the leaf.*—Smooth.

*Length and color of stipules.*—Absent of stipules.

Flower:

*Flower petal length.*—16.3 mm.

*Flower petal width.*—8.1 mm.

*Ovary shape.*—Short oval.

*Flower.*—Pollen absent.

*Flower diameter.*—About 2.3 cm to about 2.6 cm when fully opened.

*Petal length.*—About 1.58 cm to about 1.85 cm.

*Petal width.*—About 0.76 cm to about 0.95 cm.

*Petal texture.*—Smooth.

*Petal margin.*—Smooth.

*Petal color upper and lower surfaces.*—RHS NN 155 White C.

*Flower bud color.*—RHS NN 155 White C.

*Flower bud shape.*—Oval.

*Flower bud size.*—Medium.

*Flower fragrance.*—Present.

*Average number of flowers per panicle.*—About 5.

*Ovary shape.*—Short oval.

*Style length.*—About 14.5 mm to about 17.5 mm.

*Stamen number.*—About 15 to about 21, with complete style development.

*Stamen length.*—About 9.5 mm to about 14.5 mm.

*Anther color.*—White (RHS White NN155A).

*Pollinator.*—Not required.

*Parthenocarpy trait.*—Present.

*Pedicle length.*—1.1 cm.

*Pedicle color.*—RHS Yellow-Green Group 144M. In Jeju-do, Korea, the time for the first bloom is approximately March 15th, the end of bloom is approximately April 25th.

Fruit:

*Fruit shape index.*—89 to 95.

*Fruit length/width ratio.*—0.95.

*Fruit weight.*—237 g to 365 g.

*Fruit surface color.*—Medium yellow.

*Fruit surface roughness.*—Rough.

*Fruit fresh color.*—Light orange.

*Fruit flesh rate.*—72.6% to 77.7%.

*Fruit skin thickness.*—3.7 mm.

*Fruit juice total soluble solids.*—17.5° Bx.

*Fruit juice acidity.*—1.51%.

*Seed grain number.*—0.

*Mature stage.*—Late.

*Parthenocarpy.*—Present.

*Self-incompatibility.*—Present.

*Productivity of fruit.*—About 2500 kg/10 acre to about 3000 kg/10 acre.

*Market use of the fruit of the observed plant.*—Fresh fruit.

*Other fruit features.*—'Tamnaneunbong' is intermediate resistant to *citrus* scab disease and *citrus* canker, but susceptible to melanose. For the very early mature stage, 'Tamnaneunbong' should be protected when cultured. Since the fruit would be matured in the cold season, the cold season may reduce the quality of the fruit if the fruit is planted in an open field. Therefore, 'Tamnaneunbong' needs to be planted under a protected environment. Pruning on 'Tamnaneunbong' is the same as 'Shiranui'. Fruit and plant are damaged when the temperature is below −7° C.

TABLE 5

A descriptive comparison between 'Tamnaneunbong' and another known Citrus reticulate cultivar 'Setoka'(not patented).

| Variety Denomination | Harvest time | Shape Index | Sugar degree ("BX) | Acidity/ % | Fruit weight/g |
|---|---|---|---|---|---|
| Setoka | Early-Late February | 129.6 | 13 | 1.0 | 200 |
| Tamnaneunbong | Late March | 92.8 | 15.2 | 1.51 | 274.5 |

TABLE 6

The characteristic and observed dates of first and last pick in the specified location of culture as observed in Jeju-do, Korea.

| Time | Variety Denomination | Fruit weight/g | Flesh rate/% | Shape Index | Peak height/mm |
|---|---|---|---|---|---|
| 7.1.24 | Tamnaneunbong | 268.4 | 77.5 | 94 | 15.6 |
| 8.2.14 | Tamnaneunbong | 254.8 | 75.7 | 89 | 12.8 |
| 9.2.17 | Tamnaneunbong | 364.8 | 72.6 | 93 | 17.0 |
| 10.2.24 | Tamnaneunbong | 240.3 | — | — | — |
| 10.3.4 | Tamnaneunbong | 237.7 | 76.5 | 93 | — |

| Time | Pericarp thickness/mm | Seed number | Sugar degree ("BX) | Acidity/% | Acid-sugar ratio |
|---|---|---|---|---|---|
| 7.1.24 | 2.9 | 0 | 14.4 | 1.28 | 11.24 |
| 8.2.14 | 3.7 | 0 | 13.6 | 1.44 | 9.43 |
| 9.2.17 | 4.2 | 0 | 15.3 | 1.28 | 11.97 |
| 10.2.24 | — | 0 | 15.3 | 1.46 | 10.47 |
| 10.3.4 | 3.8 | 0 | 17.5 | 1.51 | 11.74 |

Regarding the observed plant's drought/heat tolerance, although the variety has not been tested for drought and heat resistance, it can grow at a temperature of about 40° C. and without irrigation for about 45 days. Such conditions do not have much effect on the growth of the variety.

What is claimed is:

1. A new and distinct cultivar of *Citrus reticulate* Blanco plant named 'Tamnaneunbong' as herein illustrated and described.

* * * * *